(12) United States Patent
Bellhouse et al.

(10) Patent No.: US 6,592,545 B1
(45) Date of Patent: *Jul. 15, 2003

(54) PARTICLE DELIVERY

(75) Inventors: Brian John Bellhouse, Oxfordshire (GB); John Bell, Oxfordshire (GB); Huw Richard Millward, Oxford (GB); Monisha Jane Phillips, Oxford (GB); Samih M. Nabulsi, Oxford (GB)

(73) Assignee: PowderJect Research Limited, Oxford (GB)

( * ) Notice: Subject to any disclaimer, the term of this patent is extended or adjusted under 35 U.S.C. 154(b) by 0 days.

This patent is subject to a terminal disclaimer.

(21) Appl. No.: 09/268,767

(22) Filed: Mar. 15, 1999

Related U.S. Application Data (63) Continuation-in-part of application No. 08/860,403, filed as application No. PCT/GB95/03016 on Dec. 21, 1995.

(30) Foreign Application Priority Data

Dec. 23, 1994 (GB) .............................................. 9426379

(51) Int. Cl.⁷ ................................................ A61M 5/30
(52) U.S. Cl. .......................................... 604/69; 604/141
(58) Field of Search ............................... 604/68–72, 88, 604/131, 139–141, 143–148, 240, 57–64

(56) References Cited

U.S. PATENT DOCUMENTS

| | | |
|---|---|---|
| 3,308,818 A | 3/1967 | Rutkowski |
| 3,595,231 A | 7/1971 | Pistor |
| 3,788,315 A | 1/1974 | Laurens |
| 4,596,556 A | 6/1986 | Morrow et al. |
| 4,691,709 A | 9/1987 | Cohen |
| 4,945,050 A | 7/1990 | Sanford et al. |
| 5,026,343 A | 6/1991 | Holzer |
| 5,049,125 A | 9/1991 | Accaries et al. |
| 5,062,830 A | 11/1991 | Dunlap |
| 5,149,655 A | 9/1992 | McCabe et al. |
| 5,204,253 A | 4/1993 | Sanford et al. |
| 5,282,785 A | 2/1994 | Shapland et al. |
| 5,330,446 A | 7/1994 | Weldon et al. |
| 5,371,015 A | 12/1994 | Sanford et al. |
| 5,630,796 A | 5/1997 | Bellhouse et al. |
| 6,010,478 A * | 1/2000 | Bellhouse et al. ............ 604/70 |

FOREIGN PATENT DOCUMENTS

| | | |
|---|---|---|
| EP | 0370571 A2 | 5/1990 |
| EP | 0406778 A1 | 1/1991 |
| EP | 0 469 814 A1 | 2/1992 |
| FR | 2 360 031 | 8/1978 |
| GB | 2 206 794 A | 1/1989 |
| GB | WO 96/25190 * | 8/1996 |
| WO | WO 92/04439 | 3/1992 |
| WO | WO 94/24263 | 10/1994 |
| WO | WO 95/19799 | 7/1995 |
| WO | WO 96/12513 | 5/1996 |
| WO | WO 96/20022 | 7/1996 |
| WO | WO 96/25190 | 8/1996 |
| WO | WO 99/04838 | 2/1999 |

OTHER PUBLICATIONS

Nabulsi et al. (1994) *Meas. Sci. Technol.* 5:267–274.

* cited by examiner

*Primary Examiner*—Brian L. Casler
*Assistant Examiner*—Michael M Thompson
(74) *Attorney, Agent, or Firm*—Thomas P. McCracken (57) ABSTRACT

A needleless syringe capable of accelerating particles into a target surface is provided. The syringe comprises a body having a lumen with a diaphragm located adjacent to a terminus thereof. Particles are delivered from an external surface of the diaphragm by means of the motive force provided by the impact of a shockwave imparted to the internal surface of the diaphragm. A method for delivering particles from the needleless syringe is also provided.

17 Claims, 8 Drawing Sheets

PARTICLE DELIVERY

CROSS-REFERENCE TO RELATED APPLICATION

This application is a continuation-in-part of U.S. patent application Ser. No. 08/860,403, filed Jun. 23, 1997, which is a 371 national stage application International Patent Application Number PCT/GB95/03016, filed Dec. 21, 1995 and designating the United States, from which applications priority is claimed pursuant to 35 U.S.C. §§120 and 365(c) and which are incorporated herein by reference in their entireties.

TECHNICAL FIELD

The present invention relates generally to a needleless syringe for use in delivering particles into a target surface. More particularly, the invention is drawn to a needleless syringe system configured for delivery of particles initially disposed upon a first surface of a diaphragm using a shockwave force that is imparted upon a second, opposing surface of the diaphragm.

BACKGROUND OF THE INVENTION

In commonly owned U.S. Pat. No. 5,630,796, a particle delivery system is described that entails the use of a needleless syringe. The syringe is used for delivering particles (powdered compounds and compositions) to skin, muscle, blood or lymph. The syringe can also be used in conjunction with surgery to deliver particles to organ surfaces, solid tumors and/or to surgical cavities (e.g., tumor beds or cavities after tumor resection).

The needleless syringe of U.S. Pat. No. 5,630,796 is typically constructed as an elongate tubular nozzle, having a rupturable membrane initially closing the passage through the nozzle adjacent to the upstream end of the nozzle. Particles, usually comprising a powdered therapeutic agent, are located adjacent to the membrane. The particles are delivered using an energizing means which applies a gaseous pressure to the upstream side of the membrane that is sufficient to burst the membrane, thereby producing a high velocity gas flow through the nozzle in which the particles are entrained.

Particle delivery using the above-described needleless syringe is typically carried out with particles having an approximate size that generally ranges between 0.1 and 250 $\mu$m. For drug delivery, an optimal particle size is usually at least about 10 to 15 $\mu$m (the size of a typical cell). For gene delivery, an optimal particle size is generally substantially smaller than 10 $\mu$m. Particles larger than about 250 $\mu$m can also be delivered from the device, with the upper limitation being the point at which the size of the particles would cause untoward damage to the target tissue. The actual distance which the delivered particles will penetrate depends upon particle size (e.g., the nominal particle diameter assuming a roughly spherical particle geometry), particle density, the initial velocity at which the particle impacts the target surface, and the density and kinematic viscosity of the target tissue (e.g., skin). In this regard, optimal particle densities for use in needleless injection generally range between about 0.1 and 25 g/cm$^3$, preferably between about 0.5 and 2.0 g/cm$^3$, and injection velocities generally range between about 100 and 3,000 m/sec.

SUMMARY OF THE INVENTION

In one embodiment of the invention, a needleless syringe is provided. The needleless syringe is capable of accelerating particles comprising a therapeutic agent across skin or mucosal tissue of a vertebrate subject. The syringe comprises, in operative combination, a body having a lumen extending therethrough. The lumen has an upstream terminus and a downstream terminus, and the upstream terminus of the lumen is interfaced with an energizing means such as a volume of a pressurized driving gas. The syringe further includes a diaphragm arranged adjacent to the downstream terminus of the lumen, wherein the diaphragm has an internal surface facing the lumen and an external surface facing outwardly from the syringe. The diaphragm is moveable between an initial position in which a concavity is provided on the external surface of the diaphragm, and a dynamic position in which the external surface of the diaphragm is substantially convex.

In certain aspects of the invention, the diaphragm is an eversible dome-shaped membrane that is comprised of a flexible polymeric material. In other aspects, the diaphragm is a bistable membrane that is moveable between an initial, inverted position and a dynamic, everted position. Particles comprising a therapeutic agent are generally housed within the concavity provided by the external surface of the diaphragm when in its initial position. The body of the needleless syringe can be configured as an elongate tubular structure with the diaphragm arranged over the downstream terminus of a lumen extending along the major axis of the tubular structure, or over an opening adjacent to the downstream terminus, which opening faces in a direction substantially perpendicular to the major axis of the tubular structure.

In another embodiment, a dome-shaped diaphragm for use with a needleless syringe is provided. The diaphragm has a concavity that sealably contains particles comprising a therapeutic agent.

In yet another embodiment of the invention, a needleless syringe is provided comprising a body having a lumen extending therethrough. The lumen has an upstream terminus and a downstream terminus, and the upstream terminus of the lumen is interfaced with an energizing means such as a volume of a pressurized driving gas. The syringe further includes a diaphragm arranged adjacent to the downstream terminus of the lumen, wherein the diaphragm has an internal surface facing the lumen and an external surface facing outwardly from the syringe. The diaphragm is moveable between an initial position in which a concavity is provided on the external surface of the diaphragm, and a dynamic position in which the external surface of the diaphragm is substantially convex. The diaphragm is characterized in that its external surface comprises one or more topographical features which selectively retain particles on the external surface of the diaphragm when in its initial, "loaded" position.

In a still further embodiment of the invention, a method for transdermal delivery of particles is provided. The method entails providing a needleless syringe according to the invention, wherein the syringe has a diaphragm with a concave surface and a convex surface, and particles are disposed on the concave surface of the diaphragm. A gaseous shock wave is released in a direction toward the convex surface of the diaphragm, wherein the shock wave provides sufficient motive force to impel the diaphragm to an everted position, thereby dislodging the particles from the diaphragm and accelerating them toward a target surface.

In certain aspects of the invention, the particles are accelerated toward the target surface in a direction substantially collinear with the direction of travel of the gaseous shock wave. In other aspects of the invention, the particles are accelerated toward the target surface in a direction transverse to the direction of travel of the gaseous shock wave.

These and other embodiments of the present invention will readily occur to those of ordinary skill in the art in view of the disclosure herein.

BRIEF DESCRIPTION OF THE FIGURES

Some examples of syringes constructed in accordance with the present invention are illustrated in the accompanying drawings, in which.

DETAILED DESCRIPTION OF THE PREFERRED EMBODIMENTS

Before describing the present invention in detail, it is to be understood that this invention is not limited to particular pharmaceutical formulations or process parameters as such may, of course, vary. It is also to be understood that the terminology used herein is for the purpose of describing particular embodiments of the invention only, and is not intended to be limiting.

All publications, patents and patent applications cited herein, whether supra or infra, are hereby incorporated by reference in their entirety.

It must be noted that, as used in this specification and the appended claims, the singular forms "a", "an" and "the" include plural referents unless the content clearly dictates otherwise. Thus, for example, reference to "a therapeutic agent" includes a mixture of two or more such agents, reference to "a gas" includes mixtures of two or more gases, and the like.

A. Definitions

Unless defined otherwise, all technical and scientific terms used herein have the same meaning as commonly understood by one of ordinary skill in the art to which the invention pertains.

The following terms are intended to be defined as indicated below.

The terms "needleless syringe," and "needleless syringe device," as used herein, expressly refer to a particle delivery system that can be used to deliver particles into and/or across tissue, wherein the particles have an average size ranging from about 0.1 to 250 $\mu$m, preferably about 10–70 $\mu$m. Particles larger than about 250 $\mu$m can also be delivered from these devices, with the upper limitation being the point at which the size of the particles would cause untoward pain and/or damage to the target tissue. The particles are delivered at high velocity, for example at velocities of at least about 150 m/s or more, and more typically at velocities of about 250–300 m/s or greater. Such needleless syringe devices were first described in commonly-owned U.S. Pat. No. 5,630,796 to Bellhouse et al., incorporated herein by reference, and have since been described in commonly owned International Publication Nos. WO 96/04947, WO 96/12513, and WO 96/20022, all of which publications are also incorporated herein by reference. These devices can be used in the transdermal delivery of a therapeutic agent into target skin or mucosal tissue, either in vitro or in vivo (in situ); or the devices can be used in the transdermal delivery of generally inert particles for the purpose of non- or minimally invasive sampling of an analyte from a biological system. Since the term only relates to devices which are suitable for delivery of particulate materials, devices such as liquid-jet injectors are expressly excluded from the definition of a "needleless syringe."

The term "transdermal" delivery captures intradermal, transdermal (or "percutaneous") and transmucosal administration, i.e., delivery by passage of a therapeutic agent into and/or through skin or mucosal tissue. See, e.g., *Transdermal Drug Delivery: Developmental Issues and Research Initiatives*, Hadgraft and Guy (eds.), Marcel Dekker, Inc., (1989); *Controlled Drug Delivery: Fundamentals and Applications*, Robinson and Lee (eds.), Marcel Dekker Inc., (1987); and *Transdernal Delivery of Drugs*, Vols. 1–3, Kydonieus and Berner (eds.), CRC Press, (1987). Aspects of the invention which are described herein in the context of "transdermal" delivery, unless otherwise specified, are meant to apply to intradermal, transdermal and transmucosal delivery. That is, the devices, systems, and methods of the invention, unless explicitly stated otherwise, should be presumed to be equally applicable to intradermal, transdermal and transmucosal modes of delivery.

As used herein, the terms "therapeutic agent" and/or "particles of a therapeutic agent" intend any compound or composition of matter which, when administered to an organism (human or animal) induces a desired pharmacologic, immunogenic, and/or physiologic effect by local and/or systemic action. The term therefore encompasses those compounds or chemicals traditionally regarded as drugs, vaccines, and biopharmaceuticals including molecules such as proteins, peptides, hormones, biological response modifiers, nucleic acids, gene constructs and the like. More particularly, the term "therapeutic agent" includes compounds or compositions for use in all of the major therapeutic areas including, but not limited to, adjuvants, anti-infectives such as antibiotics and antiviral agents; analgesics and analgesic combinations; local and general anesthetics; anorexics; antiarthritics; antiasthmatic agents; anti-convulsants; antidepressants; antigens, antihistamines; anti-inflammatory agents; antinauseants; antineoplastics; antipruritics; antipsychotics; antipyretics; antispasmodics;

cardiovascular preparations (including calcium channel blockers, beta-blockers, beta-agonists and antiarrythmics); antihypertensives; diuretics; vasodilators; central nervous system stimulants; cough and cold preparations; decongestants; diagnostics; hormones; bone growth stimulants and bone resorption inhibitors; immunosuppressives; muscle relaxants; psychostimulants; sedatives; tranquilizers; proteins peptides and fragments thereof (whether naturally occurring, chemically synthesized or recombinantly produced); and nucleic acid molecules (polymeric forms of two or more nucleotides, either ribonucleotides (RNA) or deoxyribonucleotides (DNA) including both double- and single-stranded molecules, gene constructs, expression vectors, antisense molecules and the like).

Particles of a therapeutic agent, alone or in combination with other drugs or agents, are typically prepared as pharmaceutical compositions which can contain one or more added materials such as carriers, vehicles, and/or excipients. "Carriers," "vehicles" and "excipients" generally refer to substantially inert materials which are nontoxic and do not interact with other components of the composition in a deleterious manner. These materials can be used to increase the amount of solids in particulate pharmaceutical compositions. Examples of suitable carriers include water, silicone, gelatin, waxes, and like materials. Examples of normally employed "excipients," include pharmaceutical grades of dextrose, sucrose, lactose, trehalose, mannitol, sorbitol, inositol, dextran, starch, cellulose, sodium or calcium phosphates, calcium sulfate, citric acid, tartaric acid, glycine, high molecular weight polyethylene glycols (PEG), and combinations thereof. In addition, it may be desirable to include a charged lipid and/or detergent in the pharmaceutical compositions. Such materials can be used as stabilizers, anti-oxidants, or used to reduce the possibility of local irritation at the site of administration. Suitable charged lipids include, without limitation, phosphatidylcholines (lecithin), and the like. Detergents will typically be a nonionic, anionic, cationic or amphoteric surfactant. Examples of suitable surfactants include, for example, Tergitol® and Triton® surfactants (Union Carbide Chemicals and Plastics, Danbury, CT), polyoxyethylenesorbitans, e.g., TWEEN® surfactants (Atlas Chemical Industries, Wilmington, Del.), polyoxyethylene ethers, e.g., Brij, pharmaceutically acceptable fatty acid esters, e.g., lauryl sulfate and salts thereof (SDS), and like materials.

The term "analyte" is used herein in its broadest sense to denote any specific substance or component that one desires to detect and/or measure in a physical, chemical, biochemical, electrochemical, photochemical, spectrophotometric, polarimetric, calorimetric, or radiometric analysis. A detectable signal can be obtained, either directly or indirectly, from such a material. In some applications, the analyte is a physiological analyte of interest (e.g., a physiologically active material), for example glucose, or a chemical that has a physiological action, for example a drug or pharmacological agent.

As used herein, the term "sampling" means extraction of a substance, typically an analyte, from any biological system across a membrane, generally across skin or tissue.

B. General Methods

In one embodiment of the invention, a needleless syringe device is provided having a body containing a lumen. An upstream end of the lumen is, or is arranged to be, connected to a source of gaseous pressure which can suddenly be released into the lumen. The downstream end of the lumen terminates behind an eversible diaphragm which is movable between an initial, inverted position which provides a concavity for containing particles to be delivered from the device, and an everted, outwardly convex, position. The eversible diaphragm is arranged such that, when an energizing gas flow is released into the lumen, the diaphragm will travel from its inverted to its everted position, thereby projecting the particles from the diaphragm toward a target surface.

One advantage provided by the present invention is that even when a supersonic gaseous shockwave is used as the energizing means to snap the diaphragm over from its inverted to its everted position, the diaphragm contains the gas within the lumen, preventing contact of the gas stream with the target surface. Therefore, unlike prior devices, no provision has to be made for dissipating and/or silencing a gaseous shockwave reflected from the target. Also the target surface is not subjected to the possibility of trauma or mechanical harm from the high speed gas flow.

The body can be made from any suitably resilient material, preferably from a medical-grade plastic which may be injection-molded into any desired configuration. In addition, any number of suitable energizing means can be used to power the device. For example, a chamber containing a reservoir of compressed gas can be arranged at (interfaced with) the upstream end of the lumen. The gas can be released from the energizing chamber by way of a valve, such as a spring-loaded ball valve or a piston valve, which valves are typically actuated by either mechanical means or by manual manipulation, for example, by movement of two parts of the syringe relative to each other. Alternatively, an energizing chamber can be adapted to provide for a controlled build-up of gaseous pressure from an upstream or associated (local or remote) source. For example, release of a pressurized gas flow may be achieved by building up pressure behind a rupturable membrane until the pressure difference across the membrane is sufficient to rupture the membrane and release the gas suddenly into the lumen. The velocity of the shockwave provided by these and other suitable energizing means can be increased if the driving gas is lighter than air, e.g., helium.

It is preferable, however, that the needleless syringe device is powered using a gas cylinder containing a source of compressed gas. Such gas cylinders are typically deep-drawn from aluminum or some other suitable metal or metal alloy, and find use in powering a range of other devices and appliances such as air pistols or beverage dispensers. Needleless syringe devices that are fitted with a gas cylinder are easily operated by creating a breach in a portion of the cylinder such that the compressed gas can rapidly escape therefrom. This breach can be created by the action of an actuation ram or pin which is used to snap off a frangible tip of the gas source. A number of alternative actuation mechanisms can, of course, be used to create the breach in the gas source. For example, a sharp pin or needle can be used to pierce a hole in the gas source or rupture a membrane or other relatively weak portion of the gas source. Alternatively, a trigger mechanism can be used to open a valve which closes off the gas source. These and other suitable actuation schemes and mechanisms will readily occur to the ordinarily skilled artisan upon reading the instant specification.

In order to avoid loss of particles and/or to maintain sterility of the particles prior to delivery, the concavity can be covered, for example, by a retractable shield or a thin barrier film which is readily penetrated by the particles upon delivery.

Figure 1:
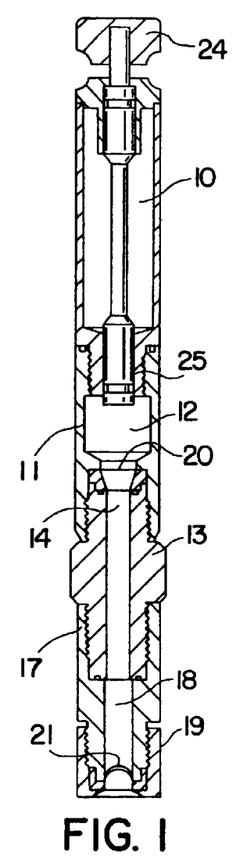
FIG. 1 is an axial section through a first embodiment of the invention.
Figure 2:
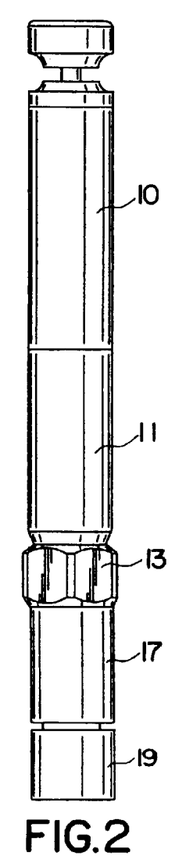
FIG. 2 is a side elevational view of the embodiment of FIG. 1.
Figure 3:
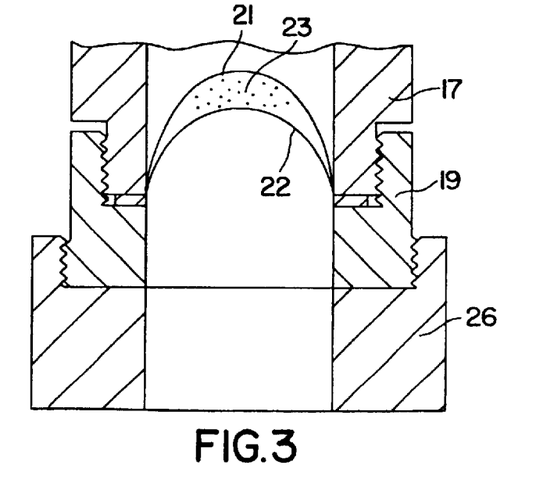
FIG. 3 is an axial section of a portion of the embodiment of FIG. 1.
Figure 4:
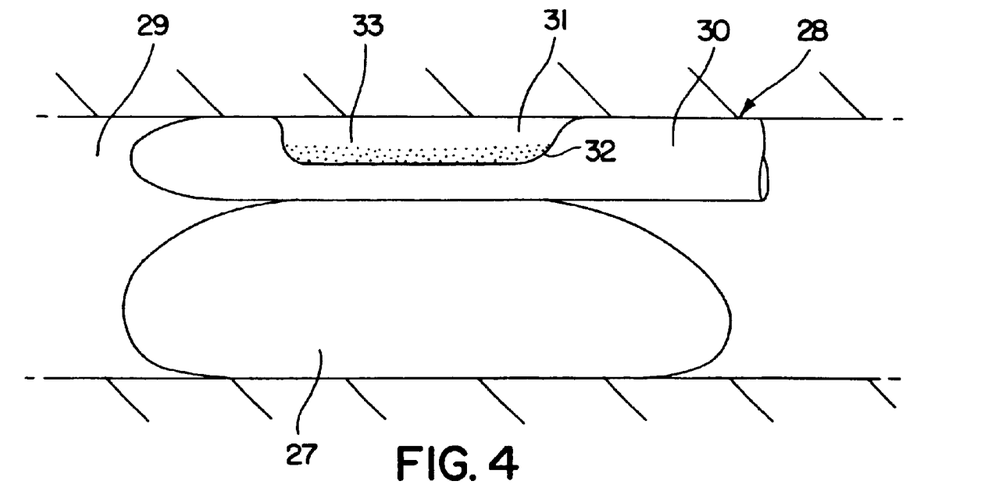
FIG. 4 is a pictorial representation of a further embodiment of the invention comprising a catheter and a positioning means.
Figure 5:
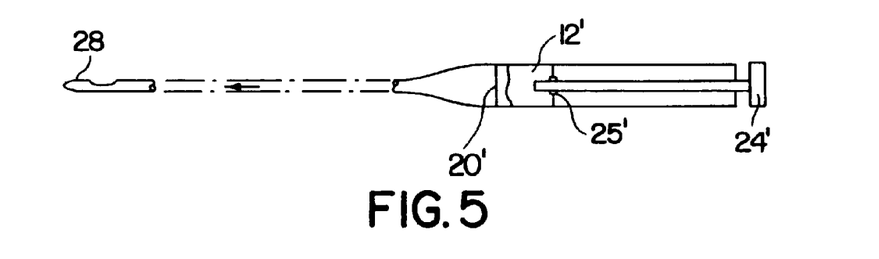
FIG. 5 is a pictorial representation of the embodiment of FIG. 4.
Figure 6:
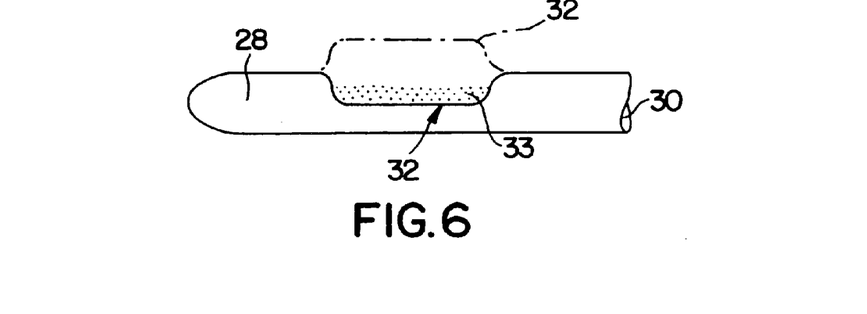
FIG. 6 is a plan side view of the tip of the embodiment of FIG. 4 showing the diaphragm in two different positions.
Figure 7:
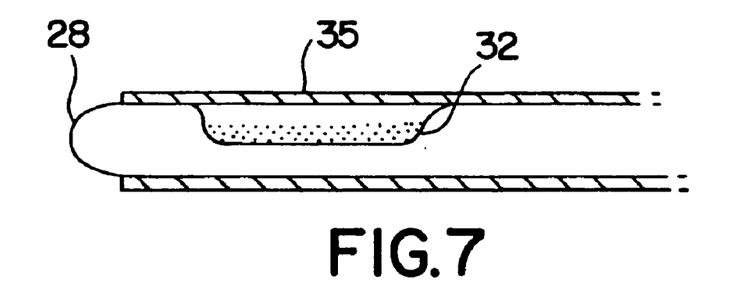
FIG. 7 is an axial section of a further embodiment of the invention.

Referring now to the accompanying drawings, FIGS. 1–3 show one embodiment of a needleless syringe suitable for transdermal delivery of particles comprising a therapeutic agent. As particularly shown in FIGS. 1 and 2, the syringe has an energizing means comprised of a cylindrical reservoir 10 initially containing helium under a pressure of about 20–80 bar. The reservoir 10 is sealably coupled to, and in fluid communication with, a first opening of tubular body portion 11 which contains a rupture chamber, indicated at 12. Connection of the reservoir to the tubular body portion can be facilitated by any suitable pressure-tight coupling. A second opening of the body portion 11 is sealably coupled to, and in fluid communication with, a second tubular body portion 13 having a passageway 14 which extends therethrough. The passageway 14 comprises an upstream terminus which interfaces with the rupture chamber 12, and a downstream terminus which interfaces with a third tubular body portion 17 when the body portion 13 is sealably coupled to the body portion 17 also by way of a pressure-tight coupler. The tubular body portion 17 contains a passageway 18, and has a tubular tip portion 19 attached thereto. The passageways 14 and 18 establish a lumen through which gasses released from the rupture chamber 12 may pass.

The particular construction of the syringe of FIGS. 1 and 2 allows the reservoir 10 to be stored separately and fitted to the rest of the syringe immediately prior to use. The body portions 11 and 13 are readily separable to allow the sandwiching between them of an optional rupturable membrane 20. The tip portion 19 is separable from the body portion 17 to allow the sandwiching between them of a diaphragm 21 which has an internal surface facing the lumen provided by the passageways 14 and 18, and an external surface facing outwardly relative to the syringe. The diaphragm 21 is moveable between an initial position in which a concavity is provided on the external surface of the diaphragm, and a dynamic position in which the external surface of the diaphragm is substantially convex. The body portions 13 and 17 are also readily separable such that one or more of the syringe components 17, 19 and 21 can be provided as a disposable unit.

Particles will initially be provided in the concavity provided by the outwardly facing external surface of the diaphragm 21. The particles may be attached to the diaphragm by electrostatic forces, by their natural sticky nature, or by way of an adhesive agent such as trehalose or silicone oil, or by the adhesive effect provided by evaporation of water or ethanol in which the particles have been suspended. Alternatively, the particles may be attached to the diaphragm by way of compacting the particles within the concavity of the diaphragm using a suitable press. The diaphragm 21 may, optionally, further comprise features on the concave side thereof, which features are useful for retaining the particles. For example, one or more annular rings, or a centrally disposed recess can be provided respectively on, or in, the external surface of the diaphragm. Such diaphragm configurations are described in detail herein below with reference to FIGS. 10–21.

Referring to FIG. 3, in the interest of sterility and/or of maintaining the integrity of the particles, the diaphragm 21 can be covered and sealed at its edge to a penetratable membrane such as a weak barrier film 22 to form a sealed capsule containing the particles 23. The weak barrier film 22 may further contain lines of weakness provided by a cut or score in the barrier to assist rupture and reduce membrane fragmentation.

The diaphragm 21 can be an eversible dome-shaped membrane that is comprised of any suitably resilient, flexible polymeric material which can withstand the impact of a shock wave provided by a gas flow traveling at supersonic speed. Exemplary materials include, for example, a polyurethane or silicone rubber material. Selection of suitable flexible dome-shaped membranes is within the capabilities of the reasonably skilled artisan upon reading this specification, wherein the flexibility of an eversible dome can be characterized by the static buckling stress provided by a particular membrane material of a given thickness. For example, the static buckling stress of a representative membrane can be determined by connecting the membrane to a high-pressure cylinder, and gradually applying increasing pressure to the convex face thereof such that the differential pressure at which the dome first begins to buckle ($P_B$) can be noted. The buckling pressure ($P_B$), then, represents the difference in pressure between the convex and concave faces at the point of buckling. The static buckling stress ($\sigma_B$) can be related to the buckling pressure ($P_B$), the effective dome radius (r), and the wall thickness (t) of the membrane, using the relationship: $\sigma_B = P_B(r)/2t$.

The buckling stress ($\sigma_B$) of a given dome-shaped membrane is strongly dependent on the dome material, but only weakly dependent on the radius (r), wall thickness (t) and the overall-dome shape. A highly flexible dome-shaped membrane can be characterized by a buckling stress ($\sigma_B$) on the order of unity when measured in units of $N/mm^2$. In this regard, the measured buckling stress of a polyurethane dome membrane suitable for use in the device of the present invention is around 0.75 $N/mm^2$, whereas a substantially rigid, inelastic dome comprised of a polyester film such as Mylar® typically has a buckling stress of at least about 23 $N/mm^2$.

Figure 8:
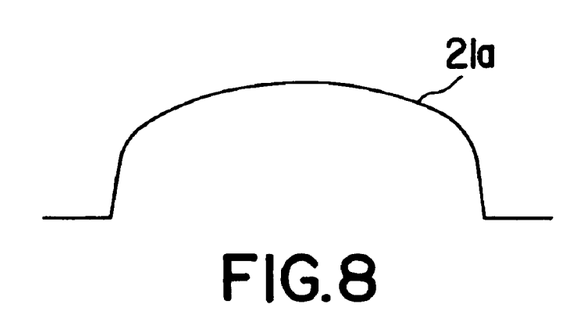
FIG. 8 is a side view of a plateau-shaped diaphragm.
Figure 9:
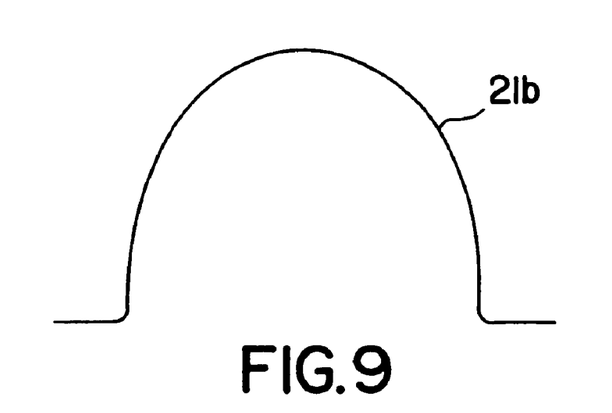
FIG. 9 is a side view of a dome-shaped diaphragm.

Flexible dome-shaped membranes used in connection with the present invention can have a number of suitable geometries, wherein the mode of dome eversion can be closely related to the geometry of the dome. Two common modes of dome eversion include (i) eversion starting at the center (axis of radial symmetry) of the dome and (ii) eversion starting at the maximum radius of the dome. Referring now to FIGS. 8 and 9, two exemplary dome geometries are depicted. The dome 21a of FIG. 8 is a plateau-shaped dome, and the dome 21b of FIG. 9 is a conventionally shaped dome. The plateau-shaped dome of FIG. 8 generally everts at a higher static buckling stress than the dome of FIG. 9.

The mode of dome eversion provided by an eversible dome-shaped membrane can be used to tailor delivery parameters, such as the size of the target area receiving the particles, and the uniformity of particle penetration into a target surface. In this regard, a plateau-shaped dome used under the same conditions as a conventional dome generally provides a more even penetration of particles that are dispersed over a wider target area. Conversely, a conventionally shaped dome can be used to concentrate particle delivery into a narrow, central region in which particle penetration is greatest at the axis of radial symmetry, subsiding radially outward therefrom.

Alternatively, the diaphragm 21 can be a bistable membrane which is shaped in the form of a dome comprised of a resilient, polymeric material such as polyester (e.g., Mylar®). The bistable membrane can be formed by thermoforming in a suitable jig.

The bistable membrane is moveable between an initial inverted position and a dynamic everted position.

In use, the needleless syringe of FIGS. 1 and 2 is assembled to provide suitable pressure-tight fittings between the components, and the lumen provided by passageways 14 and 18 is prefilled with helium at approximately atmospheric pressure. The tip 19 is placed in proximity to, or in contact with, the target skin or mucosal surface to be treated, and a plunger 24 is depressed to actuate a valve 25 to an open position which allows the pressurized helium to be discharged from the reservoir 10 and pass into the rupture chamber 12. The valve 25 may preferably be configured such that the frontal area of the plunger is greater at the downstream exit of the cylindrical reservoir 10 relative to the upstream frontal area of the plunger, resulting in a self-opening (and quick-opening) valve. When the pressure in the rupture chamber 12 has reached a sufficient value of, for example, about 23 bar, the rupture membrane 20 bursts, releasing a gaseous shockwave which propagates through the lumen formed by the passageways 14 and 18 and contacts the internal surface of the diaphragm 21. The impact of the gaseous shock wave upon the internal surface of the diaphragm provides sufficient force to suddenly impel the diaphragm from its initial position to a dynamic everted (outwardly convex) position, thereby dislodging the particles from the external surface of the diaphragm and propel them toward a target surface, simultaneously rupturing the barrier film 22. The particles are accelerated from the diaphragm at velocities sufficient for the transdermal delivery thereof across skin or mucosal tissue.

In an optional device configuration, as depicted in FIG. 3, a short tubular spacer 26 may be provided to increase the distance between the tip portion 19 and a target surface. The spacer helps ensure that the diaphragm dies not strike the target tissue, and enables the particles to become more spread out in order to increase the effective target area.

One important feature of the needleless syringe design concerns means to control the static pressure retained within the device subsequent to particle delivery. A large build-up of static pressure can be detrimental to the operability of the device when highly flexible dome-shaped membranes are employed. Thus, it is preferable that static pressure build-up is minimized or substantially eliminated. A direct way in which to minimize static pressure build-up is to increase the ratio of lumen volume-to-gas canister volume. Static pressure can also be substantially eliminated by venting the lumen to atmosphere. In this regard, such venting surprisingly does not inhibit the effectiveness of particle delivery that is attainable from the device, since the propagation of a shock wave is the key element in the eversion of the diaphragm. Thus, a vent that is substantially perpendicular with the major axis of the lumen, and having a diameter of less than half that of the lumen, is sufficient to release a driving gas after eversion of the diaphragm while not inhibiting the travel or the strength of the gaseous shock wave. Furthermore, vents arranged adjacent to the diaphragm, for example in the body part 17 or the downstream portion of body part 13, can improve the delivery performance of the needleless syringe.

Another design consideration relates to the generation of the shock wave within the needleless syringe device. For example, one way to produce a controlled shock wave is to burst a uniform rupture membrane within the syringe to release the driving gas. Rupture membranes comprised of polyester films (e.g., Mylar®) having a thickness of about 12–50 $\mu$m are adequate for these purposes. The rupture membrane initially closes-off the downstream opening of the rupture chamber 12, and a shock wave is generated once the driving gas (that has been released from the reservoir 10 or from a gas canister) reaches a critical burst pressure within the rupture chamber sufficient to rupture the membrane and allow passage of the gaseous shock wave into the lumen. Delivery performance can be optimized by increasing the rupture membrane burst pressure and/or by increasing the volume of the rupture chamber. Increases in the rupture membrane burst pressure, e.g., by increasing the thickness of a given diameter rupture membrane, provide a larger step change in pressure across the shock wave. Increased rupture chamber volume provides a concomitant increase in the mass flow, which sustains the supersonic transients of the shock wave. In order to provide sufficient mass flow through the device, the volume of the rupture chamber 12 can be substantially the same as the volume of the reservoir 10 or the volume of a gas canister.

In the device depicted in FIGS. 1 and 2, the body of the needleless syringe is configured as an elongate tubular structure, wherein the diaphragm 21 is arranged over, and closes the downstream terminus of the lumen formed by passageways 14 and 18. Upon release, the gaseous shock wave travels down the lumen and impacts the interior surface of the diaphragm, causing the acceleration of particles retained on the exterior surface of the diaphragm toward a target surface in a direction that is substantially collinear with the direction of travel of the gaseous shock wave.

In an alternative embodiment of the invention, a needleless syringe is provided which is capable of accelerating particles comprising a therapeutic agent toward a target surface in a direction transverse to the direction of travel of a gaseous shock wave. Referring now to FIGS. 4 to 7, one such device is depicted which comprises an arterial catheter and is useful for treatment of vascular proliferative disorders.

As seen in FIG. 5, a catheter is provided having at its upstream end a reservoir containing a driving gas. Release of the driving gas from the reservoir is controlled by actuation of a valve 25'. The released gas passes into a rupture chamber 12' having a rupturable membrane 20' similar to the device described herein above. The catheter may be configured as a triple lumen catheter, wherein one lumen provides the usual guidewire, the second carries gas to inflate a positional balloon 27 for urging a body 28 adjacent to the leading end (shown in FIG. 4) of the catheter against a wall of an artery 29, and the third lumen 30 is used to propagate a gaseous shockwave to the tip of the catheter.

At an opening 31 in a sidewall of the catheter body 28, there is provided a diaphragm 32 that can be comprised of an eversible, dome-shaped flexible membrane, or a bistable membrane as described above. When the diaphragm 32 is in an initial position as depicted in FIG. 4 and in solid lines in FIG. 6, the diaphragm provides a concavity in which particles 33 comprising a therapeutic agent, e.g., containing or consisting of DNA, are located. In order to avoid unwanted loss of the particles from concavity by means of the blood flow in the artery, the cavity may initially be covered by a barrier film or by a retractable sleeve 35 as shown in FIG. 7.

The catheter is used analogously to the syringe of FIGS. 1 and 2. Thus release of a driving gas from the reservoir into the rupture chamber eventually bursts the rupture membrane and causes a shockwave to be propagated along the lumen 30, causing the diaphragm 32 to travel suddenly to a dynamic, everted position as depicted in broken lines in FIG. 6, thereby propelling the particles 33 outwardly in a direction transverse to the direction of travel of the gaseous shock wave, and toward the wall of the artery 29.

Alternatively, it may be desirable for the diaphragm 32 to be housed within the peripheral envelope of the catheter body, not only when in its initial, inverted position in order to avoid interference during insertion of the catheter, but also when in its dynamic, everted position to avoid the possibility of a damaging impact with the arterial wall.

This particular embodiment of the invention is particularly useful the treatment of vascular proliferative diseases, such as for delivering genetic material into the wall of the expanded stenotic blood vessel to transform endothelial cells lining the wall of the blood vessel, and thereby preventing subsequent restenosis/re-occlusion of the blood vessel.

Moreover, the catheter-based delivery system may find other uses, for example in the localised delivery of a combination of compounds (e.g., for chemotherapy) to specific internal organs, or for local organ-based hormone replacement. The catheter device is also useful in the administration of drugs or DNA to accessible surfaces for medical purposes, for example in the treatment of tumours of mucosal surfaces, such as respiratory, gastrointestinal or genito-urinary tracts.

In accordance with another aspect of the present invention, a needleless syringe is provided having a diaphragm that provides for enhanced particle retention, wherein the external surface of the diaphragm comprises one or more topographical features that selectively retain particles on the external surface of the diaphragm when it is in an initial position. The term "topographical" is used herein in its most broad and general sense to denote the presence of any form or feature distinguishable from the surrounding substantially planar or smooth external surface of the diaphragm. Such forms or figures can be raised (e.g., in relief) or recessed with respect to the surrounding external surface of the diaphragm. One advantage of providing the external surface of the diaphragm with such topographical features is that it increases the surface area on which the particles are retained so that more, if not all, of the particles are immobilized in direct contact with the diaphragm, thereby increasing the loading capacity of the diaphragm.

The topographical features may take a wide variety of forms. For example, the features can form or otherwise comprise one or more pockets for retaining the particles. Such pockets may be formed by providing one or more grooves, channels, troughs, hollows, cavities, folds, kinks, or any conceivable combination of these or like features in the external surface of the diaphragm. Alternatively, a series of superficial cuts or scores can be made in the external surface of the diaphragm to provide the pocket(s). The features may be randomly placed about the surface of the diaphragm, or may be placed in an ordered array, for example as a series of concentric annular grooves.

An advantage of retaining the particles in one or more pockets is that when the diaphragm is in its initial position, the external surface of the diaphragm on which the particles are retained will be relatively in compression, as compared to when the diaphragm is in its dynamic position, in which the same downstream surface of the diaphragm will be comparatively in tension. In other words, during the snap eversion of the diaphragm the side walls of the pockets will tend to move apart, reducing the effective retention of the particles so that they are more freely able to be catapulted outwards toward the target surface. The effective "opening" and "closing" of the pockets as the diaphragm moves between its initial and dynamic positions may be utilized in loading the diaphragm with the particles. That is, the diaphragm can initially be manipulated into an everted "fired" position, so that the pockets are "open for reception of the particles. The diaphragm can then be gently returned to an initial "loaded" or "pre-fired" position, effectively "closing" the pockets so as to grip and selectively retain the particles. Alternatively, the diaphragm may be loaded with the particles while in its "pre-fired" position.

The topographical features may alternatively comprise one or more structures that depend from the surface of the diaphragm and extend in an outward direction from the surface. For example, one or more bristles, fingers; protrusions, ribs, fins, structural partition, rings, or any combination of these or like features can be provided on the external surface of the diaphragm. Here again, the features may be randomly placed on the surface of the diaphragm, or provided in an ordered array, for example arranged as a mesh, honey-comb or lattice work. These features can be injection molded into the diaphragm it self, or created by flock-spraying fibers onto the surface of the diaphragm. A further possibility is to provide a fabric or mesh on the downstream surface of the diaphragm. Particular arrays include a single, or a concentric series of annular ribs, fins or protrusions depending and extending from the external surface of the diaphragm.

In a particularly preferred embodiment, the topographical features comprise a series of projecting bristles. These bristles are particularly efficient in that they can be arranged to converge towards one another when the diaphragm is in its initial "loaded" position to selectively grip and retain the particles between them, and to diverge in the dynamic "fired" position of the diaphragm so as to efficiently release the particles. The bristles are also found to be efficient in distributing more evenly over the surface of the diaphragm a slurry containing gold or other heavy microparticles coated with therapeutic agent of interest, for example a peptide or some genetic material like a DNA.

In order to provide for an even, well spread particle distribution at the target tissue surface, any of the above diaphragms can be provided with a central, substantially flat or planar region. Such diaphragms take on a cross-section that is in the shape of a top hat, wherein the annular flange of the section (e.g., the "brim" of the top hat) can be used to locate the diaphragm in position in the syringe. The substantially flat or planar portion assists in providing a parallel or divergent stream of particles which will impinge evenly over an adequate target surface area. It has been found that the effective target surface area over which the particles are spread will be roughly equal to or slightly greater than the area of the flat or planar region of the diaphragm.

As above, these diaphragms which include one or more topographical features can be comprised of any suitably resilient, flexible polymeric material which can withstand the impact of a shock wave traveling in the driven gas at supersonic speed. In practice, the diaphragm will normally be molded from a plastics material, such as styrene, polyurethane or a polyester-based thermoplastic elastomer such as those sold by Bayer under the tradename of DESMOPAN™ (a polyester urethane) and by DuPont under the tradename of HYTREL™. Although the diaphragm may be molded by any appropriate technique, such as compression-molding or thermoforming, precision profiling which may be needed to produce fine topographical details on the external surface of the diaphragm is best carried out using injection-molding techniques.

When the topographical features are provided by a fabric on the external surface of the diaphragm, the diaphragm may be formed by coating a fabric, such as a tightly woven nylon or polyester fabric (e.g., a fabric having warp and weft threads at a frequency of about 34 per cm) on one side with a polymer (e.g., with a polyurethane), and then molding the resultant coated fabric into a desired diaphragm configuration by thermoforming. The fabric thus provides both pockets for selectively retaining the particles, and a degree of reinforcement to the diaphragm.

If desired, the needleless syringe can be provided with a plug inserted into the concavity of the diaphragm when in its initial position in order to further ensure that the particles are not displaced from the diaphragm prior to use. The plug is then removed before firing the device. Also, in order to increase the ability of the diaphragm to securely retain the particles prior to firing, the external surface of the diaphragm may be provided with a tacky, i.e., lightly adhesive, surface or surface treatment. In this regard, a number of polymers suitable for constructing the instant diaphragms from already have natural surface tackiness, for example, Desmopan 385 and ethylene vinyl acetate (EVA). This tackiness can be enhanced by applying an adhesive coating such as trehalose or a silicone oil (e.g., a silicone dispersion manufactured by NuSil) to the external surface of the diaphragm.

Additionally, the instant needleless syringe device can be provided with structural reinforcements or other features which can help prevent unwanted burst of the diaphragm while under the strain of the shockwave or built-up pressure within the device. As described above, a vent hole (e.g., of ≦0.5 mm diameter) can be provided in the rupture chamber or shock tube to avoid excessive build-up of gas pressure behind the diaphragm. In this regard, the transient pressure upstream of the diaphragm needs to be sufficient to evert the diaphragm during particle delivery, but can be vented in this manner so as to maintain the pressure below a critical level at which the diaphragm bursts. Alternatively, one can use insert-molding or co-molding techniques to incorporate a reinforcing metal or polymeric plate or grid at the weakest points of the diaphragm in order to minimize the likelihood of diaphragm failure during device operation. A further alternative is to provide an elastic fibre reinforcement within the diaphragm material. The addition of elastic or Lycra-like fibers within the matrix of a base polymer helps to strengthen the resulting elastomer. When used for the diaphragm, such thermoplastic elastomers would not prevent the diaphragm from expanding past its final, relaxed everted position under the action of the high pressure gas but would allow the diaphragm to relax back to its "fired" position as the gas is vented. In some cases, the diaphragm could relax back to its original inverted position. A yet further alternative is to locate a stop or rigid catching grid downstream of the diaphragm in order to limit excessive travel of the diaphragm as it snaps into its dynamic everted position, thus preventing burst, and also to maximize the rate of deceleration of the diaphragm to ensure release of the particles at the highest possible velocity. The stop or catching grid may have a similar profile to the diaphragm in its "fired" position and take the form of a shaped, perforated colander.

Figure 10:
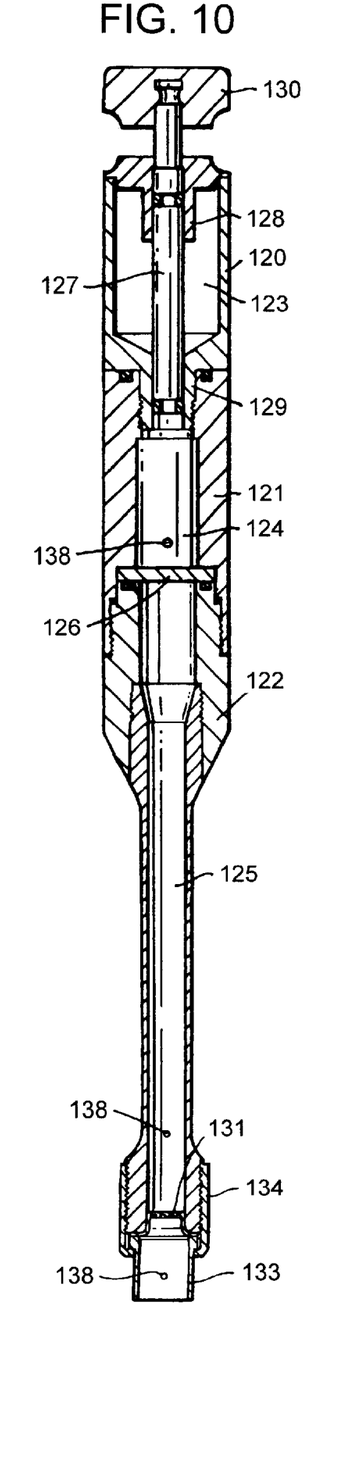
FIG. 10 is an axial section through a first embodiment of the invention.

Referring now to FIG. 10, a needleless syringe constructed according to the present invention is shown that comprises three barrel portions 120, 121 and 122 which are connected and sealed together in axial alignment. The connection of these barrel portions can be by way of any suitable pressure-tight fit couplings and can further be held in place by pins, detents or other corresponding key- or snap-fit locking mechanisms. Alternatively, the barrel portions can be screwed together using corresponding threaded couplings. The upper barrel portion 120 provides a reservoir 123 which is initially filled with an energizing gas (e.g., helium or some other suitable gas) that is at a pressure on the order of about 20–80 bar, typically about 3° bar. The intermediate barrel portion 121 includes a rupture chamber 124. The lower barrel portion 122 comprises an elongate body having a lumen extending therethrough. The upstream terminus of the lumen interfaces with the reservoir 123 by way of the rupture chamber 124. Furthermore, the lumen extending through the lower barrel portion 122 includes an elongate shock tube 125. Pinched and sealed around its edge between the upper and intermediate barrel portions 121 and 122 is a rupturable membrane 126 (shown of exaggerated thickness for clarity). The barrel portions are generally comprised of a suitably resilient material, for example, an injection-molded medical-grade polymer.

A valve stem 127 extends through the reservoir 123 and is slidable through bosses 128 and 129 to which it is initially sealed by O-rings which it carries about its periphery. The end of the valve stem 127 which projects out of the top of reservoir 123 supports an operating button 130.

A diaphragm 131 is positioned at the downstream terminus of the lumen which extends through the barrel portion 122 (the diaphragm 131 is shown as having a top hat section with a peripheral flange 132). The flange is clamped between the lower end of the barrel portion 122 and the upper end of a tubular spacer 133 which is drawn up to the barrel portion by a gland nut 134. The diaphragm therefore closes off the passage through the lumen formed by the shock tube 125.

Figure 11:
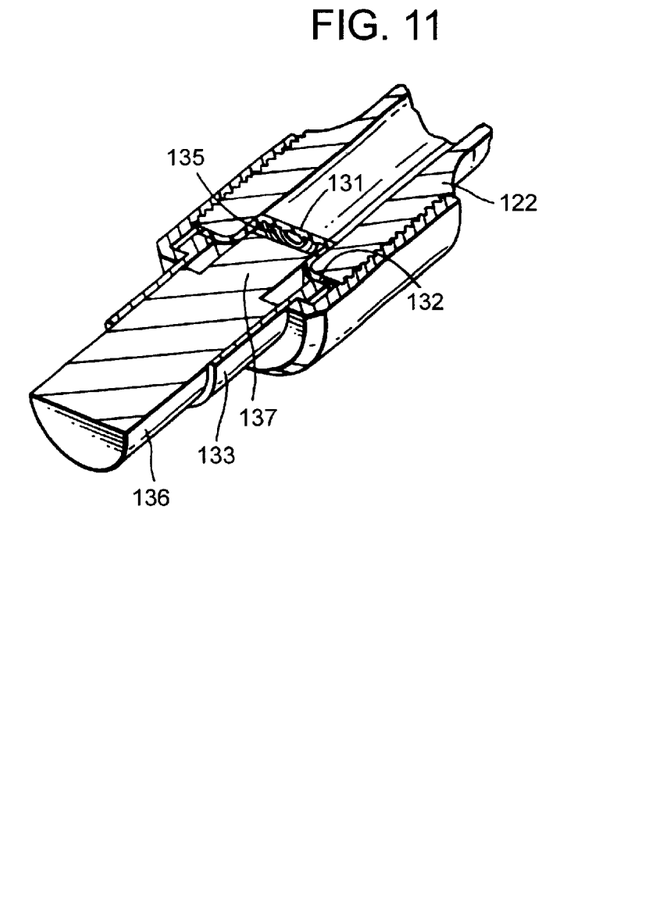
FIG. 11 is a sectional perspective view of the lower part of the syringe of FIG. 10 with the addition of a safety plug.
Figure 12A:
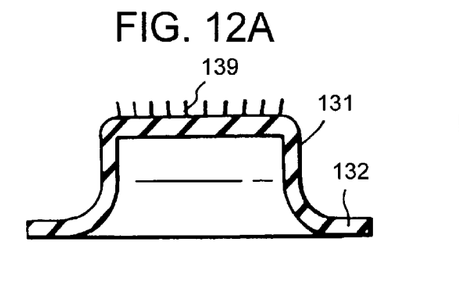
FIGS. 12–23 are diagrammatic representations of different diaphragm embodiments.
Figure 12B:
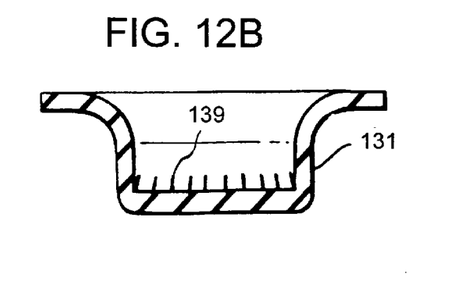
Figure 13A:
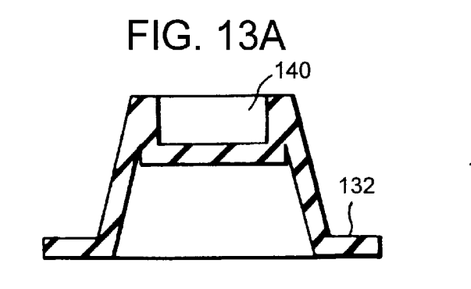
Figure 13B:
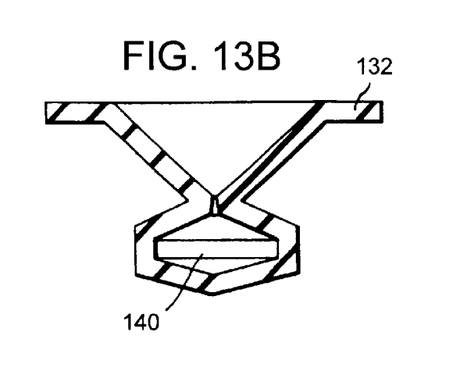
Figure 13C:
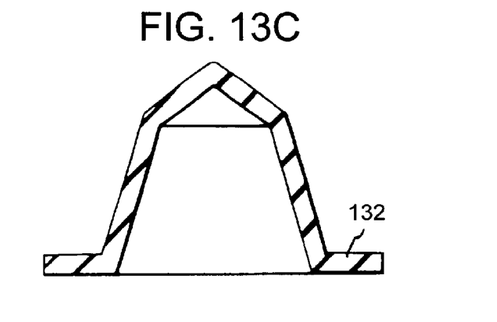
Figure 14:
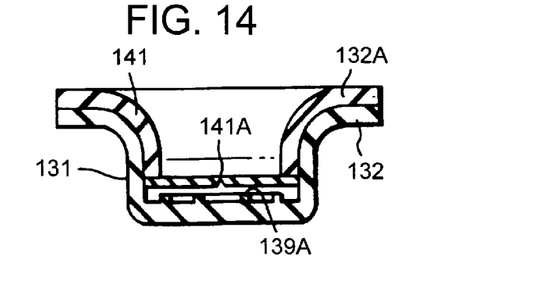
Figure 15:
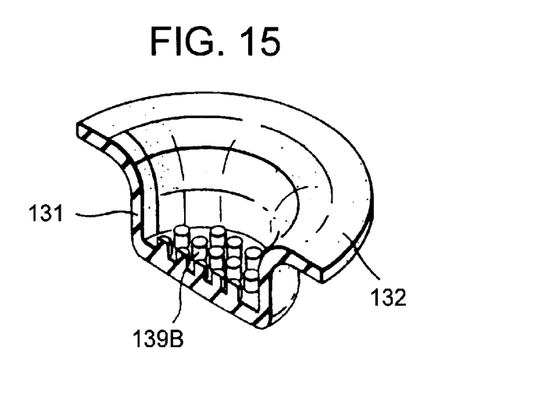
Figure 16:
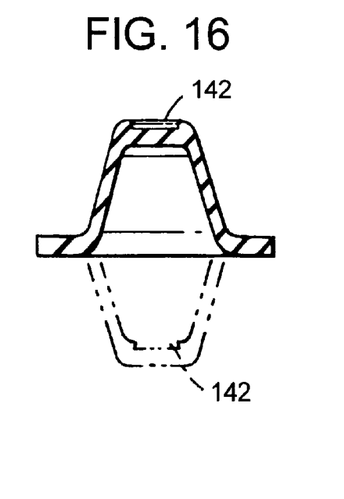
Figure 17:
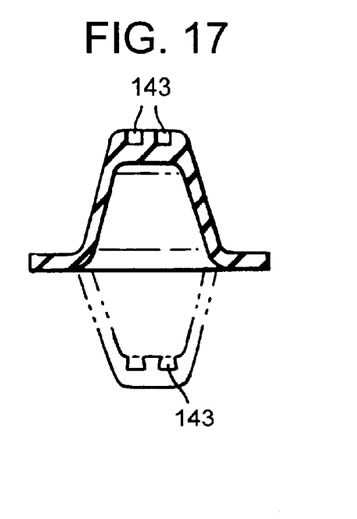
Figure 18:
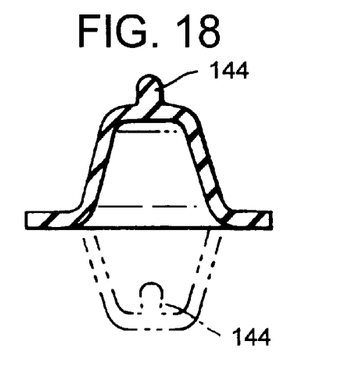
Figure 19:
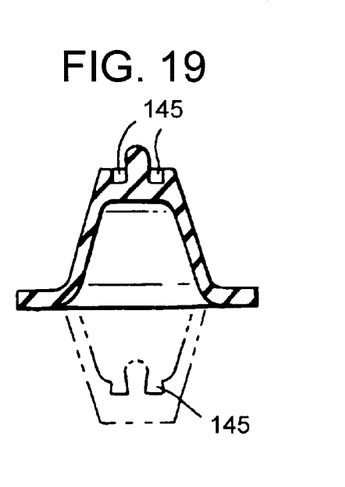
Figure 20:
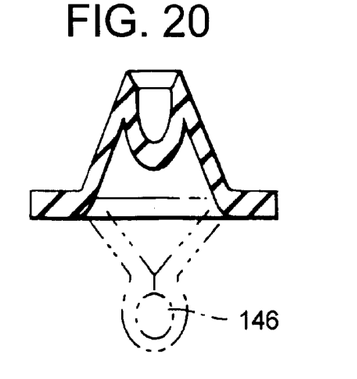
Figure 21A:
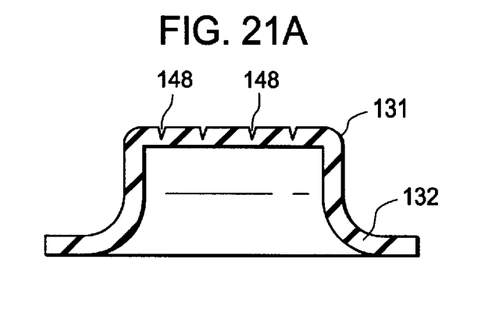
Figure 21B:
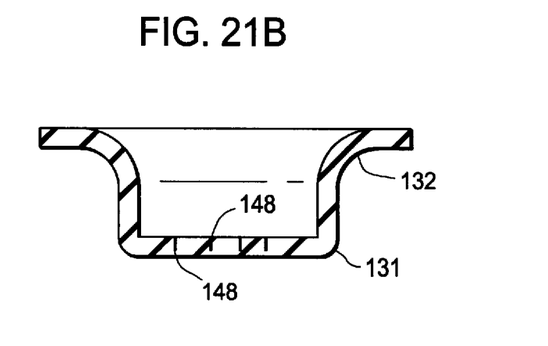
Figure 22:
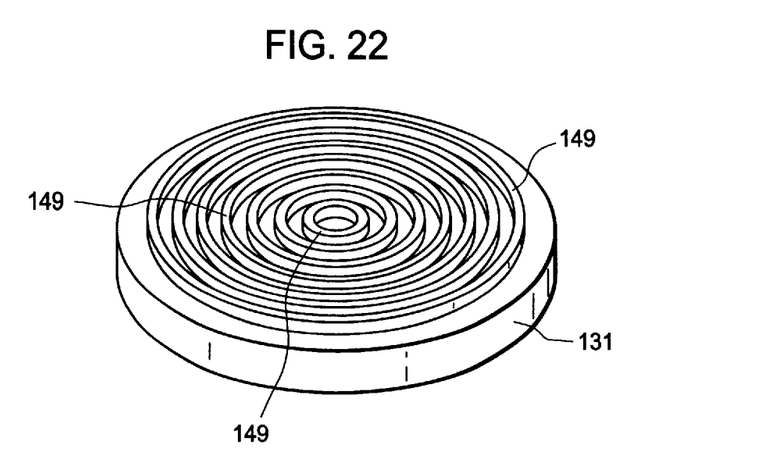
Figure 23:
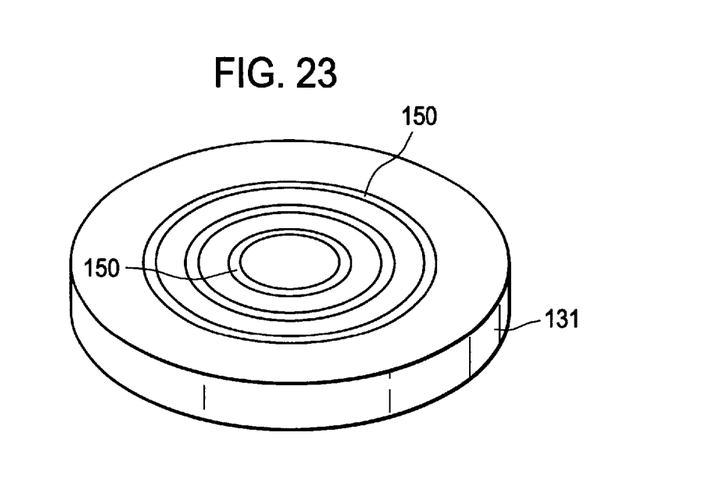
Figure 24:
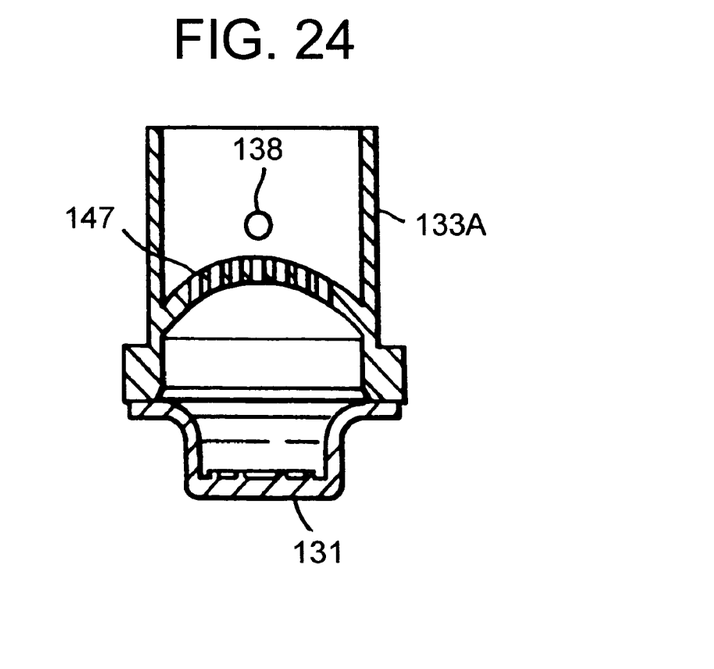
FIG. 24 is an axial section through the lower part of a syringe such as that of FIG. 10, and shows a catching grid.
Figure 25:
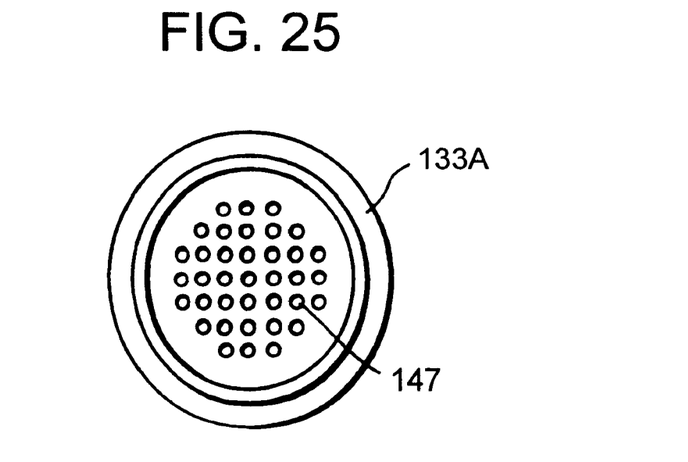
FIG. 25 is an elevation as seen in the axial direction of the parts shown in FIG. 24.

The external surface of the diaphragm comprises one or more topographical features for initially retaining particles. As can be seen in FIG. 11, the particular topographical features in this device are in the form of a series of concentric annular ribs 135, wherein the annular spaces between the concentric ribs form pockets for retaining particles on the surface of the diaphragm. As discussed above, an optional plug may be fitted in the concavity of the diaphragm to avoid displacement of the particles during transportation and handling prior to carrying out the particle delivery operation. One such plug 136, which is push fit within the spacers 133 and has a reduced end portion 137 abutting the external surface of the diaphragm, is shown in FIG. 11. The plug may be used to push and further retain the particles into the pockets of the diaphragm when the diaphragm is loaded and in its initial "pre-fired" position.

In use, the needleless syringe of FIGS. 10 and 11 is assembled to provide suitable pressure-tight fittings between the components, and the shock tube 125 can optionally be pre-charged with a driven gas (for example air or carbon dioxide) at approximately atmospheric pressure (1 bar) or slightly higher (e.g., 2–3 bar). It is preferred, but not necessary, that the driven gas in the shock tube be heavier than the driving gas that is released from the energizing means. The plug 136 is removed, and the open end of the spacer 133 placed in proximity to, or in contact with, the target skin or mucosal surface to be treated. The button 130 is depressed, driving the valve stem 127 from its seat, thus releasing the pressurized driving gas from the reservoir 123 into the rupture chamber 124. The maximum stroke of the stem 127 (before the button 130 abuts the end of the barrel portion 120) is sufficient to allow the lower sealing ring to pass from its seat in the boss 129 into the rupture chamber 124 but not sufficient for the upper sealing ring to pass out of the boss 128 into the reservoir 123. When the pressure in the rupture chamber 124 has reached a sufficient value the rupturable membrane 126 bursts, releasing a gaseous shockwave which propagates through the shock tube 125 and contacts the internal surface of the diaphragm 131. The speed at which the reservoir 123 empties into the rupture chamber is not critical, but eventually the pressure in the rupture chamber 124 and the consequential differential pressure across the membrane 126 causes the membrane to rupture and to release a supersonic shock wave along the shock tube 125. The impact of the gaseous shock wave upon the internal surface of the diaphragm provides sufficient force to suddenly impel the diaphragm from its initial position to a dynamic everted (outwardly convex) position, thereby dislodging the particles from the external surface of the diaphragm and propelling them toward the target surface. The particles are accelerated from the diaphragm at velocities sufficient for the transdermal delivery thereof across skin or mucosal tissue. A short tubular spacer 133 is provided to ensure that the diaphragm does not strike the target tissue, and to enable the particles to become more spread out and thus increase the effective target area. The spacer 133, shock tube 125, and/or rupture chamber 124 may each be provided with a vent hole 138 for releasing residual pressure from the device after firing.

Referring now to FIGS. 12–23, various exemplary diaphragm constructions are depicted. For example, FIGS. 12A–12B show a diaphragm 131 having an overall configuration in the shape of a top hat. FIG. 12A shows the diaphragm in its "start," i.e., as molded, and "fired" position. The annular peripheral flange 132 provides a lip that can be clamped between two parts of a needleless syringe (e.g., between portions 125 and 133 of the device of FIGS. 10–11), and the diaphragm is thus mounted in a syringe as described with reference to FIGS. 10 and 11. On its substantially flat, external surface, the diaphragm is integrally molded with a plurality of bristles 139 which are increasingly radially outwardly divergent towards the edge. After the particles have been located on the external surface, about the bristles, the diaphragm is gently inverted into the "loaded" position as shown in FIG. 12B. As can be seen, this causes the bristles to converge radially inwardly to an increasing extent towards the edge of the array. The particles are thus held to a significant extent by the disposition of the bristles until the diaphragm is suddenly everted to the "fired" position whereupon the particles are catapulted outwards.

FIGS. 13A–13C show a more complicated diaphragm configuration, of which FIG. 13A shows the diaphragm in its "start" position with an open pocket 140 ready to be charged with particles. FIG. 13B shows the "loaded" position in which the pocket 140 is substantially completely closed, and FIG. 13C shows the "fired" position. In this embodiment, the topographical feature (i.e., the pocket 140) comprises both the recessed pocket and surrounding kinks or folds which allow the diaphragm to fold back on itself in the loaded position and closely retain the particles.

FIG. 14 shows a diaphragm 131 in its initial, "loaded" position and having an array of bristles 139A depending and extending from the external surface of the diaphragm. The particles, which are contained within the pocket provided by the topographical features are further initially retained by a plug which is in the form of a stopper 141 and is of similar shape to the diaphragm 131. This allows for a tight fit of the stopper within the diaphragm. In addition, the stopper 141 has a peripheral flange 132A which corresponds with the peripheral flange of the diaphragm and thus can be retained in the downstream end of the shock tube in the same way as the diaphragm in FIGS. 10 and 11. The substantially flat central portion of the top hat section of the stopper 141 is provided with one or more lines of weakness 141A that allow this stopper to break apart and readily move with the diaphragm as it everts, thus substantially not impeding the catapulting of the particles from the exterior surface of the diaphragm. The stopper 141 therefore acts as an alternative to the plug 136 shown in FIG. 11 and does not have to be handled prior to use of the syringe.

FIG. 15 shows schematically, and in its initial, "loaded" position, a modification of the diaphragm of FIG. 12, in which the bristles 139B are more robust and stubby than those indicated in FIG. 12. FIGS. 16–23 show still further alternative diaphragm configurations comprising topographical features on their external surfaces, where each diaphragm is shown in its molded and dynamic "fired" position in full lines, and in their initial, "loaded" position in chain dotted lines. Whereas the diaphragms of FIGS. 12–15 and 21–23 are typically circularly symmetrical, it is possible for the diaphragms of FIGS. 16–20 to be somewhat elongate with the section being taken across the narrow dimension.

In particular, the diaphragm depicted in FIG. 16 has a centrally disposed hollow 142 that forms a pocket for selectively retaining particles on the external surface of the diaphragm when it is in its initial, "loaded" position. The diaphragm of FIG. 17 comprises topographical features that form one or more pockets, wherein the particular features are either a single groove 143 (e.g., annular) or a plurality of groove(s). The diaphragm of FIG. 18 contains a finger projection or rib 144 that depends from the external surface of the diaphragm and extends outwardly therefrom. The diaphragm of FIG. 19 is similar to that of FIG. 18, except that it has, on each side of the finger or rib 144, one or more grooves 145 (e.g., when the diaphragm includes a finger 144, a single annular groove 145 is used to establish a pocket in combination with the finger, and when the diaphragm includes a rib 144, a plurality of grooves 145 are used to establish a plurality of pockets in combination with the central rib). The diaphragm of FIG. 20 comprises kinks or folds which serve to establish a pocket 146 which is substantially closed while the diaphragm is in its initial "loaded" position.

The diaphragm of FIGS. 21A–21B comprises several superficial cuts or scores 148 on its external surface which provide pockets for selectively retaining particles. When the diaphragm is in its "fired" position, the cuts open up to accept the particles as shown in FIG. 21A, whereas when the diaphragm is in its initial "loaded" position, the cuts are substantially closed as shown in FIG. 21B. The diaphragm of FIG. 22 comprises a series of concentric fins 149 depending and extending from its external surface, while the diaphragm of FIG. 23 comprises a series of concentric grooves 150 in its external surface.

FIGS. 24 and 25 show a modified spacer 33A containing an integral perforated catching grid 47 which, as the syringe is fired and the diaphragm 31 everts, prevents over-extension and possible bursting of the diaphragm, whilst the holes in the grid substantially do not impede the catapulted particles.

Each of the needleless syringes of the present invention can be used for transdermal delivery of powdered therapeutic compounds and compositions, for delivery of genetic material into living cells (e.g., gene therapy or nucleic acid vaccination), both in vivo and ex vivo, and for the delivery of biopharmaceuticals to skin, muscle, blood or lymph. The syringes can also be used in conjunction with surgery to deliver therapeutic agents, drugs, immunogens, and/or biologics to organ surfaces, solid tumors and/or to surgical cavities (e.g., tumor beds or cavities after tumor resection). Further, the instant devices can be used in the transdermal delivery of generally inert particles for the purpose of non- or minimally invasive sampling of an analyte from a biological system. In theory, practically any agent that can be prepared in a substantially solid, particulate form can be safely and easily delivered using the present devices.

Delivery of particles from the above-described needleless syringe systems is generally practiced using particles having an approximate size generally ranging from 0.1 to 250 µm. For drug delivery, the optimal particle size is usually at least about 10 to 15 µm (the size of a typical cell). For gene delivery, the optimal particle size is generally substantially smaller than 10 µm. Particles larger than about 250 µm can also be delivered from the devices, with the upper limitation being the point at which the size of the particles would cause untoward damage to the skin cells. The actual distance which the delivered particles will penetrate a target surface depends upon particle size (e.g., the nominal particle diameter assuming a roughly spherical particle geometry), particle density, the initial velocity at which the particle impacts the surface, and the density and kinematic viscosity of the targeted skin or mucosal tissue. In this regard, optimal particle densities for use in needleless injection generally range between about 0.1 and 25 g/cm$^3$, preferably between about 0.9 and 1.5 g/cm$^3$, and injection velocities can range from about 150 to about 3,000 m/sec.

When nucleic acid preparations, e.g., DNA molecules, are to be delivered using the devices of the present invention, the preparations may optionally be encapsulated, adsorbed to, or associated with, carrier particles. Suitable carrier particles can be comprised of any high density, biologically inert material. Dense materials are preferred in order to provide particles that can be readily accelerated toward a target over a short distance, wherein the particles are still sufficiently small in size relative to the cells into which they are to be delivered.

In particular, tungsten, gold, platinum and iridium carrier particles can be used. Tungsten and gold particles are preferred. Tungsten particles are readily available in average sizes of 0.5 to 2.0 µm in diameter, and are thus suited for intracellular delivery. Gold is a preferred material since it has high density, is relatively inert to biological materials and resists oxidation, and is readily available in the form of spheres having an average diameter of from about 0.2 to 3 µm.

C. Experimental

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

EXAMPLE 1

Transmucosal Delivery of Testosterone

Testosterone and its derivatives have been given orally for the treatment of hypogonadal men (Niesschlag et al. (1976) *Hormone Research* 7:138–145; Skakkebaek et al. (1981) *Clinical Endocrinol.* 14:49–61; and Gooren, L. (1986) *Intern, J. Androl.* 9:21–26). The "first-pass" effect limits the effectiveness of testosterone treatment when administered orally, where the testosterone is absorbed entering the hepatic circulation and immediately degraded by the liver (98% first pass degradation). Moreover, a major drawback of oral androgenic therapy compared to parenteral treatment is the exposure of the liver to high androgen loads, increasing the likelihood of undesirable effects on, for example, lipid metabolism (Conway et al., (1988) *Int. J. Androl.* 112:47–64; and Thompson et al., (1989) *JAMA* 261:1165–1168).

Thus, the following study was carried out to assess the transmucosal delivery of testosterone using a needleless syringe constructed in accordance with the present invention.

Testosterone (Sigma Chemicals) was milled and sieved into a particle size range (approximately 50–100 µm) suitable for transmucosal delivery from a needleless syringe using standard stainless steel mesh sieves. Female New Zealand White rabbit subjects weighing between 2.2–2.8 kg were used and allowed food and water ad libitum. The rabbits (n=8) were randomly assigned to one of two treatment groups. The first treatment group received testosterone (2.0 mg dose) as a suspension in 35% polyvinylpyrrolidone C-30 in water (6 mg/g testosterone concentration) via subcutaneous injection. The second treatment group received testosterone (2.0 mg dose of testosterone particles ranging from 53–75 µm) as two 1.0 mg transmucosal administrations from an OralJect™ needleless syringe device abutted against the cheek mucosa.

Whole blood (1.0 ml) was taken at times 0, 0.5, 1, 2, 4, 6, 8, 12, 24 and 48 hours, the serum aspirated and assayed for testosterone by radioimmunoassay (DPC). The OralJect™ device is a prototype device of the present invention that is actuated by helium at 40 bar.

The results of the study are depicted below in Table 1 which shows the mean results and ranges for each treatment group from the study. As can be seen, testosterone bioavailability in the order of 48.3% was achieved following OralJect™ transmucosal delivery with a $t_{max}$ of 30 minutes in all animals. $C_{max}$ (the mean maximum serum concentration) was not significantly different between treatments although there was a tendency for it to be lower following OralJect™ administration. A second minor peak of serum testosterone was evident at 12 hours post administration suggesting a possible depot effect following transmucosal delivery of testosterone by the OralJect™ device.

TABLE 1

| Treatment | Subcutaneous | OralJect ™ |
| --- | --- | --- |
| $C_{max}$ nmol/I | 34.8 ± 6.9 | 25.5 ± 3.5 |
| $C_{max}$ range nmol/I | 26.9 – 55.2 | 177 – 33.5 |
| % BA† | NA | 48.3 |

†% bioavailability

These data demonstrate that it is possible to deliver a hydrophobic drug such as testosterone transmucosally using the device of the present invention. The pharmacokinetic profile observed for such delivery was markedly different from that achieved following subcutaneous administration of the same formulation of testosterone.

EXAMPLE 2

Delivery of a Powdered Local Anaesthetic to Oral Mucosa Using a Needleless Syringe Device The following studies were carried out to assess the effectiveness of transmucosal delivery to oral mucosa using a device constructed in accordance with the present invention, to provide a comparison between such delivery and a conventional needle-syringe injection, and to assess the anaesthetic effect provided by transmucosal delivery.

A randomized, double-blind, negatively controlled study was carried out in normal, healthy human subjects as follows. Initially, a single 3 mg dose of lignocaine HCL particles sized between 38 and 53 μm was delivered from a needleless syringe constructed in accordance with the invention. The lignocaine was delivered to the oral mucosa adjacent to the number 12 and 22 lateral incisors in 14 trial subjects. The delivery sites were then visually assessed for evidence of damage or irritation to the mucosal tissues. In all subjects, no evidence of any tissue reaction was observed 24–48 hours after delivery.

In a second study, a single 3.0 mg dose of lignocaine HCL particles (as above) was delivered using a needleless syringe, and a single 0.2 mL dose of 2% lignocaine HCL was delivered via needle-syringe injection. Pain associated with the administration of each treatment was scored in all 14 subjects using a 100 mm visual analogue scale immediately after each treatment, wherein 100% indicates a painful treatment, and 0% indicates a pain-free treatment. The needleless syringe employed in the study was operated using 40 bar helium driving gas to expel anaesthetic particles from a flexible, eversible dome-shaped membrane comprised of a 400 $\mu$m, 6 mm polyurethane film. The mean values of all 14 scores were: 2.4% for the needleless syringe-based procedure, and 49.9% for the needle-syringe injection, indicating that the delivery methods of the present invention are virtually painless relative to conventional injection techniques.

A randomized, double-blind study was then carried out as follows. Treatments were given to 14 subjects over the course of three visits. The treatments provided to the subjects in each visit were either a single 3.0 mg dose of Lignocaine HCL particles from the above-described needleless syringe device, or 0.0 mg (as a blinded negative control). Accordingly, treatments provided over the course of the three visits were either: two actual (3.0 mg) doses of the anaesthetic particles and one placebo; or two placebos and one actual (3.0 mg) dose. Pain stimulus was provided by probing oral mucosa with the back of a 27G dental needle, wherein the probe sequence was a probe on an untreated area of the mucosa, and then a probe on the treated area of the mucosa 1 minute post delivery. Again, the pain associated with the probe of the untreated and treated areas was scored on visual analogue scales using the above scoring methods immediately after each probe.

The mean values of all pain response scores were: 55.6% for the control (untreated) probe; 30.6% for the placebo treated probe; and 15.0% for the actual treated probe. These results demonstrate a superior level of local anaesthesia relative to the placebo treatments.

Accordingly, novel needleless syringe delivery systems and methods for using the same are disclosed. Although preferred embodiments of the subject invention have been described in some detail, it is understood that variations can be made without departing from the spirit and the scope of the invention as defined by the appended claims.

We claim:

1. A needleless syringe for accelerating particles into a target tissue surface of a vertebrate subject, said syringe comprising:

(a) a body having a lumen therein, wherein said lumen has an upstream terminus and a downstream terminus and the upstream terminus of the lumen is capable of interfacing with an energizing means; and (b) a diaphragm arranged adjacent to the downstream terminus of the lumen, said diaphragm having an internal surface facing the lumen and an external surface, wherein said diaphragm is moveable between an initial position in which a concavity is provided on the external surface of the diaphragm, and a dynamic position in which the external surface of the diaphragm is substantially convex, characterized in that the external surface of said diaphragm comprises one or more topographical features which selectively retain particles on the external surface of the diaphragm when in its initial position.

2. The syringe of claim 1 wherein said one or more topographical features on the external surface of the diaphragm comprise a pocket for retaining particles.

3. The syringe of claim 2 wherein the pocket is provided by a groove, channel or trough in the external surface of the diaphragm.

4. The syringe of claim 2 wherein the pocket is provided by one or more superficial cuts or scores on the external surface of the diaphragm.

5. The syringe of claim 2 wherein the pocket is provided by a fold or kink in the diaphragm.

6. The syringe of claim 1 wherein said one or more topographical features on the external surface of the diaphragm comprise a structure depending and extending outwardly from the external surface of said diaphragm.

7. The syringe of claim 6 wherein the external surface of the diaphragm comprises one or more bristles depending from the diaphragm and extending outwardly therefrom.

8. The syringe of claim 7 wherein the external surface of the diaphragm comprises one or more ribs, fins or structural partitions depending from the diaphragm and extending outwardly therefrom.

9. The syringe of claim 7 wherein the external surface of the diaphragm comprises one or more annular ribs, fins or structural partitions depending from the diaphragm and extending outwardly therefrom.

10. The syringe of claim 1 wherein a central region of the external surface of the diaphragm is substantially flat or planar.

11. The syringe of claim 1 wherein the diaphragm has an overall configuration in the shape of a top hat.

12. The syringe of claim 1 wherein the diaphragm is reinforced with a fabric attached or adhered to the internal or external surface of the diaphragm.

13. The syringe of claim 1 further comprising a stop arranged at or over the downstream terminus of the lumen such that said stop prevents excess travel of the diaphragm as it moves to its dynamic, outwardly convex position.

14. The syringe of claim 1 wherein the lumen comprises an elongate cylindrical shock tube.

15. The syringe of claim 14 wherein the shock tube comprises an aperture for venting gases therefrom.

16. The syringe of claim 14 further comprising a rupture chamber having a first opening adapted to interface with an energizing means, and a second opening which is in fluid communication with the upstream terminus of the lumen.

17. The syringe of claim 16, wherein the second opening of the rupture chamber is closed by a rupturable membrane.

* * * * *